United States Patent [19]

Herrmann et al.

[11] Patent Number: 5,663,451
[45] Date of Patent: Sep. 2, 1997

[54] PROCESS FOR PREPARING ALDEHYDES

[75] Inventors: Wolfgang A. Herrmann, Freising; Martina Elison, München; Jakob Fischer, Kirchdorf; Christian Köcher, München, all of Germany

[73] Assignee: Hoechst Aktiengesellschaft, Germany

[21] Appl. No.: 581,399

[22] Filed: Dec. 29, 1995

[30] Foreign Application Priority Data

Dec. 29, 1994 [DE] Germany ............... 44 47 067.3

[51] Int. Cl.$^6$ ................................................. C07C 45/50
[52] U.S. Cl. ................................... 568/451; 568/454
[58] Field of Search ............................. 568/451, 454

[56] References Cited

PUBLICATIONS

Hendrickson et al; Organic Chemistry;Third Edition;p. 345 1970.
Tanaka, et al, Chemical Abstracts, vol. 87, No. 25 (1977), No. 200792.

Primary Examiner—C. Warren Ivy
Assistant Examiner—Sreeni Padmanabhan
Attorney, Agent, or Firm—Bierman, Muserlian & Lucas

[57] ABSTRACT

A process for the hydroformylation of olefins and olefinically unsaturated compounds in the presence of cobalt or rhodium complexes which contain, as complexing ligands, heterocyclic carbenes and, if desired, further ligands.

18 Claims, No Drawings

PROCESS FOR PREPARING ALDEHYDES

This Application claims the priority of German Application P 44 47 067.3, filed Dec. 29, 1994.

The Invention relates to a process for the preparation of aldehydes by hydroformylation of olefins in the presence of complexes of cobalt or of rhodium which contain heterocyclic carbenes as ligands. The reaction of olefins with carbon monoxide and hydrogen can be carried out either in a homogeneous or in a heterogeneous phase.

BACKGROUND OF THE INVENTION

It is known that reaction of olefins with carbon monoxide and hydrogen (hydroformylation) can be used to prepare aldehydes and alcohols which contain one carbon atom more than the starting olefin. The reaction is catalyzed by hydridometal carbonyls, preferably of the metals of groups 8, 9, and 10 of the Periodic Table (corresponding to the IUPAC recommendation of 1985). Apart from cobalt, which was originally used as the catalyst metal and has been widely used in industry, rhodium has recently been gaining increasing importance. In contrast to cobalt, rhodium allows the reaction to be carried out at low pressure. In addition, terminal olefins preferentially form n-aldehydes and only lesser amounts of isoaldehydes. Finally, the hydrogenation of the olefins to give saturated hydrocarbons is also significantly lower in the presence of rhodium catalysts than with cobalt catalysts. In the processes introduced in industry, the rhodium catalyst is used in the form of modified hydridorhodium carbonyls which contain additional ligands, in particular tertiary organic phosphines or phosphites. The cobalt catalysts are also used in the form of carbonyls which additionally contain phosphines or phosphites as ligands, even though this variant of the hydroformylation is of lesser industrial importance than processes in which rhodium serves as catalyst.

The ligands which control the activity of the catalyst metal (also referred to as control ligands) are usually present in excess of the amount required for formation of the complex, and thereby stabilize the complex by the law of mass action. The catalyst system therefore comprises a complex and free a ligand, and the ligand is important, not only for the specific catalytic activity, but also for the stability of the complex.

The hydroformylation reaction can be carried out either in homogeneous or in heterogeneous systems. In the homogeneously catalyzed reaction, the catalyst is dissolved in the reaction product and a solvent may also be present. This procedure has proven itself well both when using cobalt catalysts and when using rhodium catalysts. However, difficulties are presented in the separation of the reaction products and, in the case of the reaction catalyzed by rhodium, in the recovery of the catalyst. Product and catalyst solutions are customarily separated from one another by distillation. However, owing to the thermal sensitivity of the aldehydes and alcohols formed, this route can only be used in the hydroformylation of lower olefins, i.e. olefins having up to about 8 carbon atoms in the molecule.

The indicated deficiencies are avoided in the rhodium-catalyzed reaction by using water-soluble rhodium complexes as catalysts. Such a process is described, for example, in DE-C 26 27 354. The solubility of the rhodium complexes is here achieved by use of sulfonated triarylphosphines as constituents thereof. In this embodiment, separation of the catalyst from the reaction product after the reaction is complete is carried out simply by separation of aqueous and organic phases, i.e., without distillation, and thus without additional thermal process steps. A further feature of this procedure is that n-aldehydes are formed with particularly high selectivity from terminal olefins, and isoaldehydes are formed only in very much smaller amounts. The complexing constituents used for water-soluble rhodium complexes are preferably sulfonated triarylphosphines and additionally carboxylated triarylphosphines.

Organic phosphines, regardless of whether they are soluble in organic media or in water, have proven themselves well in industrial practice as control ligands owing to their wide variety, their catalytic activity, and their selectivity. Nevertheless, a series of disadvantages stands in the way of their wider use. These include, in particular, the oxidation sensitivity which occurs especially in the presence of metals and metal ions. Therefore, when using catalysts based on phosphine-containing complexes, measures have to be taken to exclude oxidizing agents such as oxygen or air so as to reduce the losses of the ligands, which can frequently only be prepared at high cost. A further property which all organic phosphines have in common, which limits their possible uses, is the irreversible cleavage of phosphorus-carbon bonds; for example, in hydroformylation this occurs to an increased extent above certain temperatures depending on the type of phosphine. It leads to deactivation of the catalyst and thus to high phosphine consumption which impairs the economics of the method. Finally, the conventional alkylphosphines and arylphosphines, like the organic phosphites similarly used as ligands, do not allow coverage of the entire range of the electronic control possibilities in respect of the catalytically active metal centers. In particular, there is a lack of strongly nucleophilic electron-rich ligands which are resistant to oxidizing agents and form stable bonds to the metal.

SUMMARY OF THE INVENTION

It is, therefore, an object of the Invention to develop new metal complexes as catalysts for the hydroformylation reaction, which metal complexes do not have the indicated disadvantages and, in addition, can be easily and inexpensively synthesized. Further, it should be possible to vary the constitution of the control ligands in a simple manner so that catalysts matched to individual catalytic problems can be prepared.

This object is achieved for a process for the preparation of aldehydes by reaction of monoolefins, polyolefins, cycloolefins, or derivatives thereof with carbon monoxide and hydrogen. The reaction takes place at temperatures of 20° to 180° C. and pressures of 0.1 to 30 MPa in the presence of complexes of cobalt or of rhodium as the catalyst. In the process, the complexes have the formula $$[L_a M_b X_c]^p (A)_n \qquad (I)$$

wherein M is cobalt or rhodium as the central atom, X is a monodentate or multidentate, charged or uncharged ligand bound to the central atom, and L is also ligands bound to the central atom M and is a monocarbene of the formula

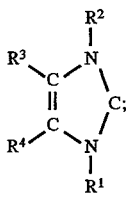
(II)

and

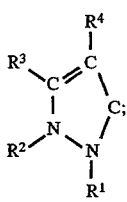
(III)

or a dicarbene of the formula

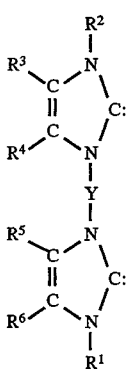
(IV)

and

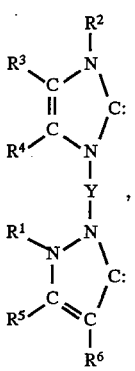
(V)

wherein $R^1$, $R^2$, $R^3$, $R^4$, $R^5$, and $R^6$ are individually straight or branched chain, sulfonated or unsulfonated alkyls having 1 to 7 carbon atoms, sulfonated or unsulfonated aliphatic monocyclics or polycyclics having 5 to 18 carbon atoms, sulfonated or unsulfonated alkenyls having 2 to 5 carbon atoms, sulfonated or unsulfonated aryls having 6 to 14 carbon atoms, or sulfonated or unsulfonated aralkyl radicals having 7 to 19 carbon atoms. $R^1$ and/or $R^2$ can also be —$(CH_2)_mPR_2$, wherein m=1, 2, 3, or 4 and R=benzyl, phenyl, substituted phenyl, naphthyl, —$(CH_2)_mNR'_2$ (wherein m is as defined above and R'=alkyl, vinyl, allyl, benzyl, aryl), and —$(CH_2)_mOR''$ (wherein m is as defined above and R''=alkyl, in particular methyl, vinyl, allyl, benzyl, or phenyl). $R^3$, $R^4$, $R^5$, and $R^6$ can also be hydrogen; $R^3$ together with $R^4$, and $R^5$ together with $R^6$, can individually be fused and sulfonated or unsulfonated radicals having 3 to 7 carbon atoms. $R^1$, $R^2$, $R^4$, or $R^6$ together with ligand X can form a ring, Y is saturated or unsaturated, straight or branched chain alkylidene having 1 to 4 carbon atoms, dialkylsilylene, or tetraalkyldisilylene; A is a singly charged anion or the chemical equivalent of a multiply charged anion, b is an integer from 1 to 3, a is an integer from 1 to 4 times b, c=0 or an integer from 1 to 4 times b, and n=0 or an integer from 1 to 6.

DETAILED DESCRIPTION OF THE INVENTION

X is a monodentate or multidentate ligand which can be present in the complexes, in addition to the carbenes, selected from the group consisting of hydrogen, hydrogen ion, halogens, halide ions, pseudohalides, carboxylate ions, sulfonate ions, alkyls having 1 to 7 carbon atoms, amides, alkoxides, acetylacetonates, carbon monoxide, nitrogen monoxide, nitriles, isonitriles, monoolefins, diolefins, alkynes, and π-aromatic radicals. If a plurality of these ligands is present in the molecule of the complex, they can be the same or different.

In the monocarbenes or dicarbenes corresponding to Formulas (II), (III), (IV) and (V), which are derived from imidazole and from pyrazole or their derivatives, $R^1$ to $R^6$ are desirably methyl, isopropyl, tert-butyl, benzyl, triphenylmethyl, phenyl, tolyl, xylyl, mesityl, and/or adamantyl. $R^1$ and $R^2$ are preferably methyl, tert-butyl, phenyl, benzyl, and/or o-tolyl; $R^3$ and $R^4$ are preferably hydrogen and/or methyl.

$R^3$ and $R^4$ and $R^5$ and $R^6$ can, together with two adjacent carbon atoms of the imidazole ring or the C—N moiety in the pyrazole ring, form a ring system. $R^3$ and $R^4$ or $R^5$ and $R^6$ are then preferably the moieties $(CH)_4$ thus leading to the formation of a fused aromatic six-membered ring; $(CH_2)_4$; and $(CH_2)_5$.

The bridges denoted by Y are preferably methylene, dimethylmethylene, diphenylmethylene, 1,3-phenylene, and ethylidene. Among the silicon-containing bridges, the dimethylsilylene and tetramethyldisilylene are preferred.

a is preferably 1 or 2, b is preferably 1; n is preferably a number from 0 to 3. A is preferably halide, pseudohalide, tetraphenylborate, tetrafluoroborate, hexafluorophosphate, or carboxylate ion; particularly acetate, and a metal complex anion such as, for example, tetracarbonylcobaltate, hexafluoroferrate(III), tetrachloroferrate, tetrachloroaluminate, or tetrachloropalladate(II).

The cobalt and rhodium complexes used as catalysts can be obtained by various routes. One preparative method starts out from simple compounds, i.e., salts or metal complexes (such as the acetylacetonates, metal carbonyls) of each element which forms the central atom of the complex. According to a variant, the new compounds are obtained from complexes by ligand exchange or by elimination and/or substitution reactions, for example, from the usual solvent complexes of these metal compounds. The compounds claimed can also be obtained by simple addition of the carbene to the respective metal component, with this molecular addition also being able to occur with breaking up of the bridge structure.

The carbenes are used, depending on their stability, either in free form, as a solution or, more frequently, prepared in the reaction mixture from compounds which can be converted into carbenes under the reaction conditions. The most important method of formation is the deprotonation of imidazolium or pyrazolium salts, if desired by addition of bases such as metal hydrides, carbonyl-metallates, metal carboxylates, metal alkoxides, or metal amides.

The reaction of the starting materials, i.e. the simple salts or the complexes, with the carbenes (and further ligands, if desired) is carried out by mixing the reactants in a solvent at room or elevated temperature. The reaction proceeds rapidly and is often essentially complete after a few minutes. However, to ensure completeness of the reaction, it is advisable to employ reaction times of up to a number of hours, particularly when the starting materials are only partially dissolved in the medium used, i.e. they react from suspension. To prepare water-soluble complexes containing sulfonated ligands, the starting materials include at least one reactant whose molecule or molecular fragment is sulfonated.

To isolate the new complexes from the reaction medium, it has been found to be useful to evaporate the solvent, advantageously under high vacuum. The crude product is purified by washing and recrystallization from a suitable solvent or solvent mixture which can be selected in the individual case by preliminary experiments.

The cobalt and rhodium complexes used are soluble in organic solvents and in water (as salts), particularly when they contain aliphatic or aromatic radicals substituted by sulfonic acid groups. They are very thermally stable and frequently stable even at temperatures above 350° C. In addition, it is notable that they undergo oxidation reactions only with difficulty, in contrast to phosphines and phosphites. Finally, the complexes do not tend to dissociate. It is therefore frequently not necessary to use the ligands for controlling catalyst activity and stability in an excess over the stoichiometric amount required for formation of the complex. If it is found to be advantageous to use an excess of ligand, this can be significantly less than when using phosphines or phosphites.

Depending on their solubility, the catalytically active complexes of cobalt or rhodium can be used homogeneously dissolved in the organic reaction medium which usually comprises the starting olefin, the reaction product, reaction byproducts, and possibly a solvent. They can also be used as a separate phase in aqueous solution in a heterogeneous reaction system. Particularly suitable water-soluble catalysts are complexes containing heterogeneous carbene ligands substituted by sulfonic acid groups.

The cobalt or rhodium complexes are generally synthesized prior to the actual reaction, but they can also be prepared in situ in the reaction mixture of the hydroformylation. In both cases, the catalysts are obtained as described above from salts or complexes of the metals cobalt or rhodium. Under the action of synthesis gas, the cobalt or rhodium complexes originally used are converted into the active hydroformylation catalyst.

The concentration of the metal (in the form of the complex) in the organic or aqueous catalyst solution is, based on olefinically unsaturated compound used, from $10^{-6}$ to 1 mol %, preferably from $10^{-4}$ to $10^{-1}$ mol %. Within the ranges indicated, the cobalt concentration required is up to ten times that of the rhodium concentration required.

The reaction of the olefinically unsaturated compound with carbon monoxide and hydrogen is carried out at pressures of about 0.1 to about 300 MPa, preferably from 1 to 15 MPa, with cobalt catalysts requiring higher pressures than rhodium catalysts. The composition of the synthesis gas, i.e. the volume ratio of carbon monoxide and hydrogen, can extend over a wide range, for example, from 1:10 to 10:1. In general, use is made of gas mixtures in which the volume ratio of carbon monoxide to hydrogen is about 1:1 or deviates only slightly from this value in either direction.

The reaction temperature is between about 20° and 180° C., preference being given to 80° to 150° C. Cobalt catalysts require higher temperatures than catalysts based on rhodium.

The reaction of the reactants present in a liquid or gaseous phase is carried out in conventional reactors. The course of the reaction is decisively influenced by intimate contact between, in the case of the homogeneous systems, a liquid and a gaseous phase and, in the case of the heterogeneous systems, two liquid phases and a gaseous phase. It is therefore necessary to generate as large as possible a contact surface between the phases. Thus, synthesis gas and, if desired, the olefin are preferably fed into the liquid phase via distribution devices. In the case of the hydroformylation reaction carried out using a heterogeneous catalyst phase, it is advisable to stir the reaction mixture intensively. If desired, a solubilizer can also be added to the aqueous phase to improve the solubility of the olefinic compound in the catalyst. The reaction can be carried out batchwise or, preferably, continuously.

The process of the Invention can be successfully applied to the reaction of monoolefins, polyolefins, cyclic olefins, and derivatives of these unsaturated compounds. With regard to the molecular size, the olefins used are subject to no restriction; the procedure has been found to be successful for compounds having from 2 to 40 carbon atoms. The olefinically unsaturated compounds can be straight or branched chain and the double bonds can be terminal or internal. Examples of olefins which can be used in the new process are ethylene, propylene, 1-butene, 2-butene, 1-pentene, 2-methylbutene-1, 1-hexene, 2-hexene, 1-heptene, 1-octene, 3-octene, 3-ethylhexene-1, 1-decene, 3-undecene, 4,4-dimethylnonene-1, dicyclopentadiene, vinylcyclohexene, cyclooctadiene, styrene, and 2-vinylnaphthalene. Derivatives of the types of olefins specified which can be hydroformylated using the method claimed are, for example, alcohols, aldehydes, carboxylic acids, esters, nitriles, and halogen compounds; more specifically, allyl alcohol, acrolein, methacrolein, crotonaldehyde, methyl acrylate, ethyl crotonate, diethyl fumarate, diethyl maleate, and acrylonitrile, are suitable. The process is used with particular success for the hydroformylation of olefins and olefin derivatives having from 2 to 20 carbon atoms.

If one of the carbene ligands is chiral, i.e., it possesses no symmetry element of the second type according to the Schönflies system, asymmetric inductions occur in the hydroformylation products if the starting materials are prochiral and the metal complex catalyst is used in optically pure form. Chiral products can be prepared in this way.

In the following, the preparation of the new catalysts is first described; the subsequent examples illustrate the Invention but do not restrict it.

EXAMPLE 1

Preparation of chloro($\eta^4$-1,5-cyclooctadiene)(1,3-dimethylimidazolin-2-ylidene)rhodium(I) (Catalyst 1)

a) 1,3-Dimethylimidazolin-2-ylidene 8.69 g (38.8 mmol) of 1,3-dimethylimidazolium iodide is dissolved, together with 1.03 g (42.7 mmol) of sodium hydride and 0.2 g (1.8 mmol) of potassium tert-butoxide, in 50 ml of tetrahydrofuran (THF) and stirred for 4 hours at room temperature in a Schlenk tube having an attached paraffin oil nonreturn valve. The solution is turned yellow by the free carbene formed. The solvent is evaporated under high vacuum and the residue is vacuum distilled in a microdistillation apparatus. This gives 1,3-dimethylimidazolin-2-ylidene in the form of a yellow oil. The carbene was immediately dissolved in 60 ml of THF and stored at −30° C.

b) Chloro($\eta^4$-1,5-cyclooctadiene)(1,3-dimethylimidazolin-2-ylidene)rhodium(I)

247 mg (0.5 mmol) of di($\mu$-chloro)bis($\eta^4$-1,5-cyclooctadiene)dirhodium is dissolved or suspended at room temperature in 20 ml of absolute THF and the resultant mixture was mixed with 92 mg (1 mmol) of 1,3-dimethylimidazolin-2-ylidene. The immediate reaction can be recognized by a color change from pale yellow to deep yellow. The mixture is stirred for a further 15 minutes at room temperature, the solvent is evaporated under high vacuum, and the residue is purified by washing with 10 ml of diethyl ether. The product is dissolved in 10 ml of methylene chloride and carefully covered with 30 ml of pentane. The resulting yellow crystals are freed of the solvent mixture by decantation and dried in a high vacuum. The compound dissolved readily in chloroform and methylene chloride, dissolved well in THF and toluene, dissolved sparingly in diethyl ether and pentane, giving a yellow color. Even after heating in moist toluene for a number of hours in an oxygen atmosphere, no decomposition took place. Yield: 310 mg (91%).

From 5.0 to 20.0 mg (from 0.015 to 0.058 mmol) of this compound were used as catalyst (see Table).

EXAMPLE 2

Preparation of [($\eta^4$-1,5-cyclooctadiene)-bis(1,3-dimethylimidazolin-2-ylidene)rhodium(I)] chloride (Catalyst 2)

247 mg (0.5 mmol) of di($\mu$-chloro)bis($\eta^4$-1,5-cyclooctadiene(dirhodium is dissolved or suspended at room temperature in 20 ml of absolute THF and mixed with 279 mg (3 mmol) of 1,3-dimethylimidazolin-2-ylidene. The immediate reaction is recognized by a color change from pale yellow to deep yellow. The mixture is stirred for a further 3 hours at room temperature, the solvent is evaporated under high vacuum, and the residue is purified by washing with 30 ml of diethyl ether. The product is dissolved or suspended in 10 ml of methylene chloride and carefully covered with 10 ml of pentane. The resulting yellow crystals are freed of the solvent mixture by decantation and dried under high vacuum. The compound is readily soluble in chloroform and methylene chloride; moderately soluble in THF, water, and toluene; and insoluble in diethyl ether and pentane. Yield: 410 mg (93%).

From 5.0 to 20.0 mg (from 0.011 to 0.046 mmol) of this compound is used as catalyst (see Table).

EXAMPLE 3

In situ preparation of Catalyst 3
a) 1-Methyl-3-(ethylsulfonic acid sodium salt) imidazolium bromide 205 mg (2.5 mmol) of methylimidazole is stirred without a solvent with 210 mg (1 mmol) of 2-bromoethanesulfonic acid sodium salt for three days at 70° C. After cooling, the residue was washed three times with 30 ml of diethyl ether to remove excess methylimidazole. After drying under high vacuum (70° C., 10 hours), a white solid remained which is very readily soluble in water, and slightly soluble in organic solvents (such as THF, toluene, pentane). Yield: 280 mg (96%).
b) Catalyst 3

100 mg of rhodium(III) acetate (0.357 mmol) is dissolved in 25 ml of degassed water and mixed with a solution of 314 mg of 1-methyl-3-(ethyl-2-sulfonic acid sodium salt) imidazolium bromide (1.07 mmol) in 25 ml of degassed water. From 1.0 to 5.0 ml (from 0.00714 to 0.0357 mmol) of this solution (rhodium content 0.0714 mmol per 10 ml of water) is used; the active hydroformylation catalyst is formed under hydroformylation conditions.

EXAMPLE 4

In situ preparation of Catalyst 4
a) 1-(Ethyl-2-sulfonic acid sodium salt)-3-(ethyl-2-sulfonate)imidazolium betaine 557 mg (8.2 mmol) of imidazole, dissolved in 20 ml of dimethylacetamide, is mixed with 1.5 ml (10.25 mmol) of triethylamine and 3.45 g (16.3 mmol) of 2-bromoethanesulfonic acid sodium salt. On heating to 120° C., the original suspension becomes clear. After further heating to 160° C., a white precipitate began to form. To achieve complete reaction, the mixture was heated for 4 hours under reflux. After cooling the solution to room temperature, the white precipitate was filtered off and washed twice with 20 ml of ethanol and ether each time.
b) Catalyst 4

100 mg of rhodium(III) acetate (0.357 mmol) is dissolved in 25 ml of degassed water and mixed with a solution of 328 mg (1.07 mmol) of 1-(ethyl-2-sulfonic acid sodium salt)-3-(ethyl-2-sulfonate)imidazolium betaine in 25 ml of degassed water. From 1.0 to 5.0 ml (from 0.00714 to 0.0357 mmol) of this solution (rhodium content 0.0714 mmol per 10 ml of water) is used as catalyst (see Table); the active hydroformylation catalyst forms under hydroformylation conditions.

EXAMPLE 5

In situ preparation of Catalyst 5
a) 1-Methyl-3(butyl-4-sulfonate) imidazolium betaine Methylimidazole (8.21 mg, 10 mmol) is stirred without solvent with 1,4-butanesultone (1361 mg, 10 mmol) at room temperature for 3 days. After solidification of the mass, it was washed 3 times with toluene and dried under high vacuum. The white solid was readily soluble in water, less readily soluble in organic solvents. Yield: 2100 mg (96%).
b) Catalyst 5

100 mg of rhodium(III) acetate (0.357 mmol) is dissolved in 25 ml of degassed water and mixed with a solution of 234 mg (1.07 mmol) of 1-methyl-3-(butyl-4-sulfonate)-imidazolium betaine in 35 ml of degassed water. From 1.0 to 5.0 ml (0.00595 to 0.02975 mmol) of this solution (rhodium content 0.0595 mmol per 10 ml of water) is used as catalyst (see Table), the active hydroformylation catalyst is formed under hydroformylation conditions.

EXAMPLE 6

In situ preparation of Catalyst 6

10.0 mg of rhodium(III) hexanoate (0.0223 mmol) and 14.6 mg of 1,3-dimethylimidazolium iodide (0.0669 mmol) are weighed into the glass insert of an autoclave and mixed with 25 ml of toluene. This suspension is used directly as catalyst (see Table), the active hydroformylation catalyst is formed under hydroformylation conditions.

EXAMPLE 7

Hydroformylation of olefins

From 1000 to 100,000 equivalents of an olefin are reacted with synthesis gas while stirring (about 150 rpm) in a 250 ml stirred autoclave (Roth Laboratory Autoclave model H 10781 with glass insert) in the presence of 5 to 20 mg of the catalyst prepared according to Examples 1 and 2 and dissolved in toluene, or from 1.0 to 5.0 ml of the aqueous catalyst solutions prepared according to Examples 3 to 5.

The synthesis gas contained $H_2$ and CO in a volume ratio of 1:1, the total pressure was 10 MPa, the propene partial pressure (when using propene as olefin) was 1.2 MPa. As soon as the pressure dropped to about 3.0 to 4.0 MPa during the course of the reaction, further synthesis gas was injected.

After cooling to room temperature, the product was analyzed by means of gas chromatography/mass spectrometry and/or purified by distillation before analysis.

TABLE

Hydroformylation of olefins

| No. | Catalyst | Olefin | Cat./olefin | Solvent | n/iso ratio | (%) | Conversion Observations |
|---|---|---|---|---|---|---|---|
| 1 | 1 | Propene | 1:100,000 | Toluene | 1.0:1.0 | >99(60 h) | |
| 2 | 1 | 1-Hexene | 1:100,000 | Toluene | 1.0:1.0 | 85(60 h) | |
| 3 | 1 | Styrene | 1:2000 | Toluene | 1.16:1.0 | 100(20 h) | |
| 4 | 1 | Tetramethylethylene | 1:1000 | Toluene | *<br>** | 82(20 h) | Isomerization of starting material |
| 5 | 1 | 2-Hexene | 1:2500 | Toluene | 1.0:1.0 | 95(20 h) | Isomerization of starting material |
| 6 | 2 | 1-Hexene | 1:2500 | Toluene | 2.0:1.0 | 85(20 h) | Catalyst sparingly soluble in toluene |
| 7 | 2 | Propene | 1:10000 | Water | 1.2:1 | 85(20 h) | Catalyst soluble in butyraldehyde phase after catalysis |
| 8 | 3 | Propene | 1:10,000 | Water | 2.1:1 | 85(20 h) | Catalyst also soluble in aqueous phase after catalysis; red |
| 9 | 4 | Propene | 1:10,000 | Water | 1.9:1 | 92(20 h) | Catalyst also dissolved in aqueous phase after catalysis; red |
| 10 | 5 | Propene | 1:10,000 | Water | 1.4:1 | 65(20 h) | Catalyst also dissolved in aqueous phase after catalysis; red |
| 11 | 6 | Propene | 1:10,000 | Toluene | 1.4:1 | 70(20 h) | |

Note to the Table
*Only 3,4-dimethylpentanal is identified in the product by means of gas chromatography/mass spectrometry.
**Only n-heptenal (33.8%) and 2-methylhexanal (66.2%) are identified as products by gas chromatography/mass spectrometry.

While only a limited number of specific embodiments of the present Invention have been expressly disclosed, it is, nonetheless, to be broadly construed and not to be limited except by the character of the claims appended hereto.

What is claimed is:

1. A process for preparing aldehydes by reaction of a compound selected from the group consisting of monoolefins, polyolefins, cycloolefins, or derivatives thereof with carbon monoxide and hydrogen at temperatures of from 20° to 180° C. and pressures of from 0.1 to 30 MPa in the presence of complexes of cobalt or of rhodium as a catalyst, wherein said complexes are of the formula $$[L_aM_bX_c]^n(A)_{n'} \quad (I)$$

wherein M is cobalt or rhodium as a central atom, X's are individually monodentate or multidentate, charged or uncharged ligands bound to said central atom and L's are individually ligands bound to said central atom and are selected from the group consisting of monocarbenes and dicarbenes of the formulas

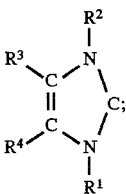
(II)

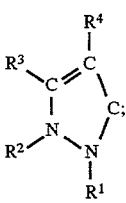
(III)

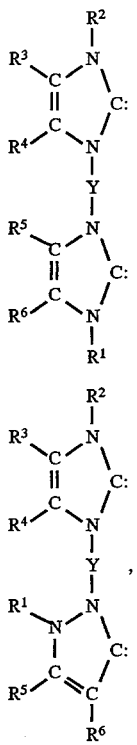

(IV)

(V)

wherein $R^1$, $R^2$, $R^3$, $R^4$, $R^5$, and $R^6$ are individually selected from the group consisting of straight or branched chain, sulfonated or unsulfonated alkyls having 1 to 7 carbon atoms; sulfonated or unsulfonated aliphatic monocyclics and polycyclics having 5 to 18 carbon atoms; sulfonated or unsulfonated alkenyls having 2 to 5 carbon atoms; sulfonated or unsulfonated aryls having 6 to 14 carbon atoms; and sulfonated or unsulfonated aralkyls having 7 to 19 carbon atoms; $R^1$ and $R^2$ are also selected from the group consisting of —$(CH_2)_mPR_2$, wherein m=1, 2, 3, or 4 and R=benzyl, phenyl, substituted phenyl, naphthyl; —$(CH_2)_mNR'_2$ (wherein R'=alkyl, vinyl, allyl, benzyl, and aryl); and —$(CH_2)_mOR''$ (wherein R''=alkyl); $R^3$, $R^4$, $R^5$, and $R^6$ can also be hydrogen; $R^3$ together with $R^4$, and $R^5$ together with $R^6$, may individually form fused and sulfonated or unsulfonated radicals having 3 to 7 carbon atoms, $R^1$, $R^2$, $R^4$, or $R^6$ together with X may form a ring, Y is selected from the group consisting of saturated or unsaturated, straight or branched chain alkylidenes having 1 to 4 carbon atoms, dialkylsilylenes, and tetraalkyldisilylenes; A is a singly charged anion or the chemical equivalent of a multiply charged anion, b is an integer from 1 to 3, a is an integer from 1 to 4 times b, and c=0 or an integer from 1 to 4 times b, and n' =0 or an integer from 1 to 6.

2. The process of claim 1 wherein R'' is selected from the group consisting of methyl, vinyl, allyl, benzyl, and phenyl.

3. The process of claim 1 wherein the X's are selected from the group consisting of hydrogen, hydrogen ion, halogens, halide ions, pseudohalides, carboxylate ions, sulfonate ions, alkyls having 1 to 7 carbon atoms, amides, alkoxides, acetylacetonates, carbon monoxide, nitrogen monoxide, nitriles, isonitriles, monoolefins, diolefins, alkynes, and π-aromatic radicals.

4. The process of claim 1 wherein $R^1$, $R^2$, $R^3$, $R^4$, $R^5$, and $R^6$ are individually methyl, isopropyl, tert-butyl, benzyl, triphenylmethyl, phenyl, tolyl, xylyl, or mesityl.

5. The process of claims 1 wherein $R^3$ and $R^4$ are individually hydrogen or methyl.

6. The process of claim 1 wherein $R^3$ together with $R^4$, and $R^5$ together with $R^6$, are individually $(CH)_4$, $(CH_2)_4$, or $(CH_2)_5$.

7. The process of claim 1 wherein Y is methylene, dimethylmethylene, diphenylmethylene, 1,3-phenylene, or ethylidene.

8. The process of claim 1 wherein Y is dimethylsilylene or tetramethyldisilylene.

9. The process of claim 1 wherein a is 1 or 2.

10. The process of claim 1 wherein b is 1.

11. The process of claim 1 wherein n is 0 to 3.

12. The process of claim 1 wherein A is halide, pseudohalide ion, tetraphenylborate ion, tetrafluoroborate ion, hexafluorophosphate ion, acetate ion, tetracarbonylcobaltate ion, hexafluoroferrate ion, tetrachloroferrate ion, tetrachloroaluminate ion, or tetrachloropalladate ion.

13. The process of claim 1 wherein said reaction is carried out in the presence of a catalyst homogeneously dissolved in a reaction medium.

14. The process of claim 1 wherein said reaction is carried out in the presence of an aqueous catalyst solution.

15. The process of claim 1 wherein a concentration of said central atom in an organic phase or in an aqueous phase is $10^{-6}$ to 1 mol %, based on said compound.

16. The process of claim 15 wherein said concentration is $10^{-4}$ to $10^{-1}$ mol %.

17. The process of claim 1 wherein said reaction is carried out at 80° to 150° C.

18. The process of claim 1 wherein said compound has 2 to 40 carbon atoms.

* * * * *